United States Patent
Sigman et al.

(10) Patent No.: US 8,088,346 B2
(45) Date of Patent: Jan. 3, 2012

(54) ALKENE HYDROFUNCTIONALIZATION REACTIONS

(75) Inventors: Matthew S. Sigman, Salt Lake City, UT (US); Keith M. Gligorich, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 828 days.

(21) Appl. No.: 12/146,304

(22) Filed: Jun. 25, 2008

(65) Prior Publication Data

US 2009/0069580 A1 Mar. 12, 2009

Related U.S. Application Data

(60) Provisional application No. 60/937,284, filed on Jun. 25, 2007.

(51) Int. Cl.
*C01G 55/00* (2006.01)
(52) U.S. Cl. .......................................................... 423/22
(58) Field of Classification Search .................. None
See application file for complete search history.

(56) References Cited

OTHER PUBLICATIONS

Gligorich et al. JACS, 2006, 128, 2794-2795.*
Norio Miyaura et al., Cross-coupling reaction of organoboron compounds via base-assisted transmetalationto palladium(II) complexes. Journal of Organometallic Chemistry 653 (2002) pp. 54-57.
Yasumasa Iwai et al., Aerobic Alcohol Oxidation Coupled to Palladuim-Catalyzed Alkene Hydroarylation with Boronic Esters. Angew. Chem. Int. Ed. 2008, 47, pp. 3219-3222.
Takashi Nishikata et al., 1,4-Addition of Arylboronic Acids and Arylsiloxanes to Unsaturated Carbonly Compounds via Transmetalation to Dicationic Palladium (II) Complexes. Organometallics 2004, 23, pp. 4317-4324.
Sherry R. Chemler et al. The B-Alkyl Suzuki-Miyaura Cross-Coupling Reaction: Development, Mechanistic Study, and Applications in Natural Product Synthesis**. Angew. Chem. Int. Ed. 2001, 40, pp. 4544-4568.
Silvina C. Pellegrinet et al., Asymmetric Conjugate Addition of Alkynylboronates to Enones: Rationale for the Intriguing Catalysis Exerted by Binaphthols. J. Am. Chem. Soc. 2006, 128, pp. 3116-3117.
Mark Lautens et al., Rhodium-Catalyzed Coupling Reactions of Arylboronic Acids to Olefins in Aqueous Media. J. Am. Chem. Soc. 2001, 123, pp. 5358-5359.
Matthew S. Sigman et al., Ligand-Modulated Palladium-Catalyzed Aerobic Alcohol Oxidations. vol. 39, No. 3, 2006 pp. 221-229.

* cited by examiner

*Primary Examiner* — Daniel Sullivan
*Assistant Examiner* — Yevegeny Valenrod
(74) *Attorney, Agent, or Firm* — Thorpe North & Western LLP

(57) ABSTRACT

A reductive cross coupling reaction process for functionalization of a nucleophilic alkene can be achieved. The nucleophilic alkene and a nucleophilic cross coupling partner compound can be reacted in the presence of an oxidizable alcohol and a suitable catalyst to form a reductive coupling product. Various additives can also be useful to refine the process such as by mitigating certain undesirable intermediates, facilitating specific site selectivity for various substitutions or reaction sites, etc. Chiral additives can be optionally used which act to provide asymmetric catalysis, e.g. allow for regioselective and stereoselective production of reductive coupling products. A reductive cross coupling pathway can include oxidizing the oxidizable alcohol to form a catalyst hydride. The nucleophilic alkene can be inserted into the catalyst hydride to form a catalyst-alkyl intermediate. Further, the catalyst-alkyl intermediate can be transmetallized with the nucleophilic cross coupling partner compound to form a transmetallated intermediate. The catalyst can be reductively eliminated to form the reductive coupling product and a reduced catalyst. Finally, the reduced catalyst can be oxidized under aerobic conditions, for example with oxygen, to form the oxidized catalyst and subsequent repetition through the cyclic pathway.

27 Claims, 4 Drawing Sheets

*A. Deuterium Labeling Experiments*

*No Deuterium Incorporation*

*B. Diene Substrate*

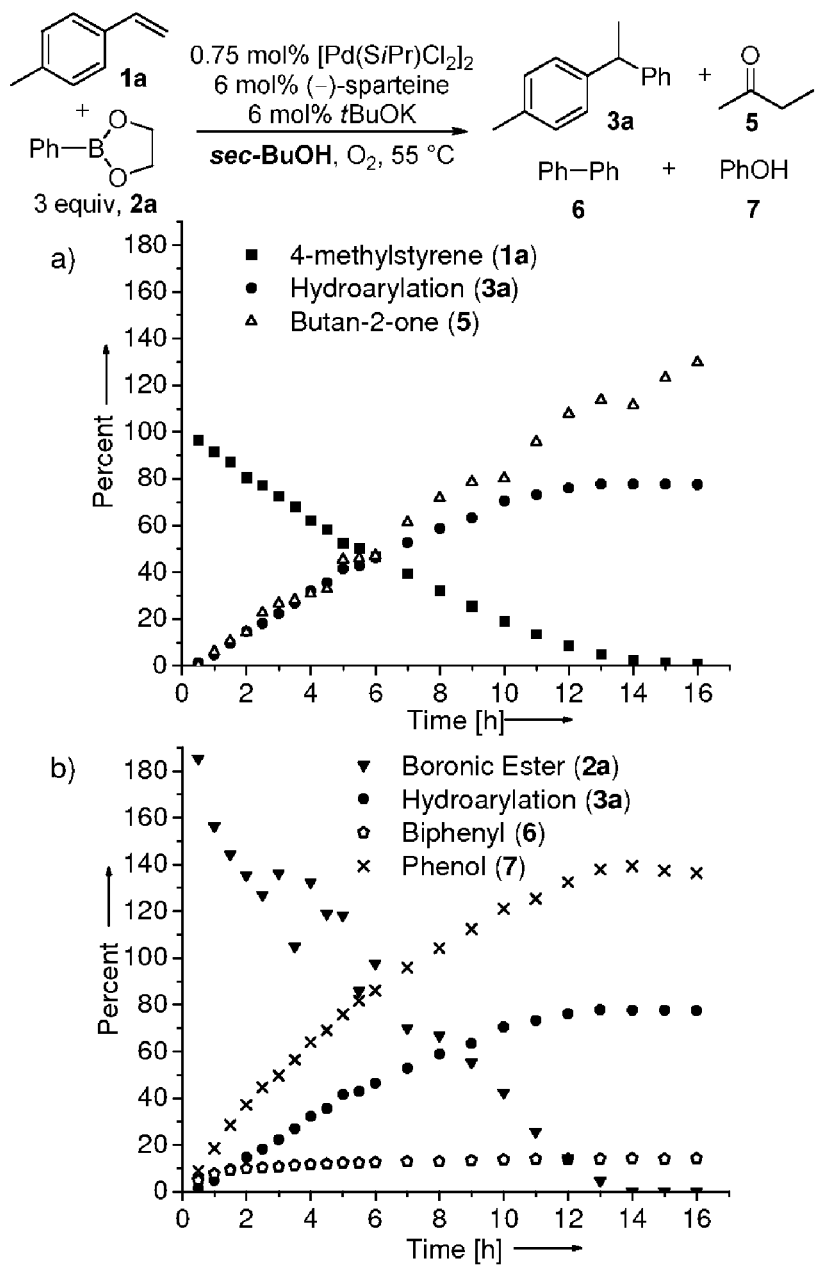
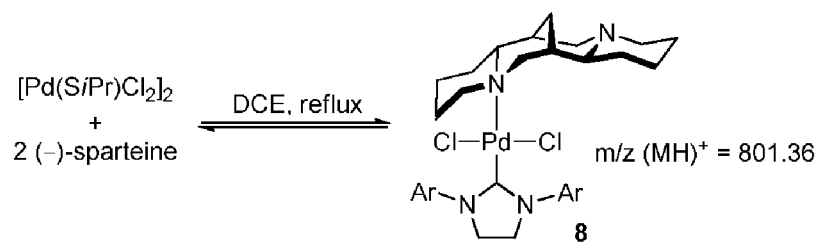
Figure 4
Figure 5

ALKENE HYDROFUNCTIONALIZATION REACTIONS

RELATED APPLICATIONS

This application claims the benefit of U.S. Provisional Application No. 60/937,284, filed Jun. 25, 2007 and which is incorporated herein by reference.

GOVERNMENT INTEREST

This invention was made with government support under NIH Grant No. GM63540 awarded by the National Institutes of Health. The Government has certain rights to this invention.

FIELD OF THE INVENTION

This invention relates generally to the field of chemical synthesis and more specifically to coupling reactions used to functionalize alkenes. Accordingly, the present invention involves the fields of chemistry and reaction engineering.

BACKGROUND OF THE INVENTION

Over the past several decades, the development of transition metal catalyzed processes has revolutionized approaches to and implementation of target synthesis. As a primary example, palladium(0)-catalyzed cross coupling of an electrophilic organic compound (generally compounds containing carbon-halogen bonds) and a nucleophilic organometallic reagent has emerged as a powerful method to construct carbon-carbon bonds. In fact, cross-coupling reactions are now relied upon for the synthesis of materials, pharmaceuticals, and natural products. Mechanistically, these reactions are thought to proceed by initial $Pd^0$ promoted oxidative addition of the electrophilic organic compound (RX) to yield an oxidized species, $R-Pd^{II}-X$ (FIG. 1A). This step is typically independent of the nucleophilic organometallic cross coupling partner. By definition, one of the cross coupling partners must be able to oxidize $Pd^0$ to $Pd^{II}$ thereby limiting the potential scope of these ubiquitous transformations. As such, reactions using palladium-catalyzed cross coupling continued to be sought through ongoing research and development

SUMMARY

It has been recognized that the ability to access $R-Pd^{II}-X$ via alternative routes, specifically using substrates that need not oxidize $Pd^0$ to $Pd^{II}$, can considerably enhance the versatility of Pd-catalyzed cross coupling reactions. In accordance with the present invention, a reductive cross coupling reaction process for functionalization of a nucleophilic alkene can be achieved. In particular, the nucleophilic alkene and a nucleophilic cross coupling partner compound can be reacted in the presence of an oxidizable alcohol and a suitable catalyst to form a reductive coupling product.

Thus, various aspects of the present invention have been outlined generally so that the detailed description that follows may be better understood and appreciated. Further, this summary is not intended to be limiting, but is rather instructive for understanding of the appended claims of associated detailed description. Departure from the examples provided in terms of specific compounds, as well as alterations may be had without departing from the scope of the invention circumscribed by the appended claims.

BRIEF DESCRIPTIONS OF THE DRAWINGS

Figure 1:
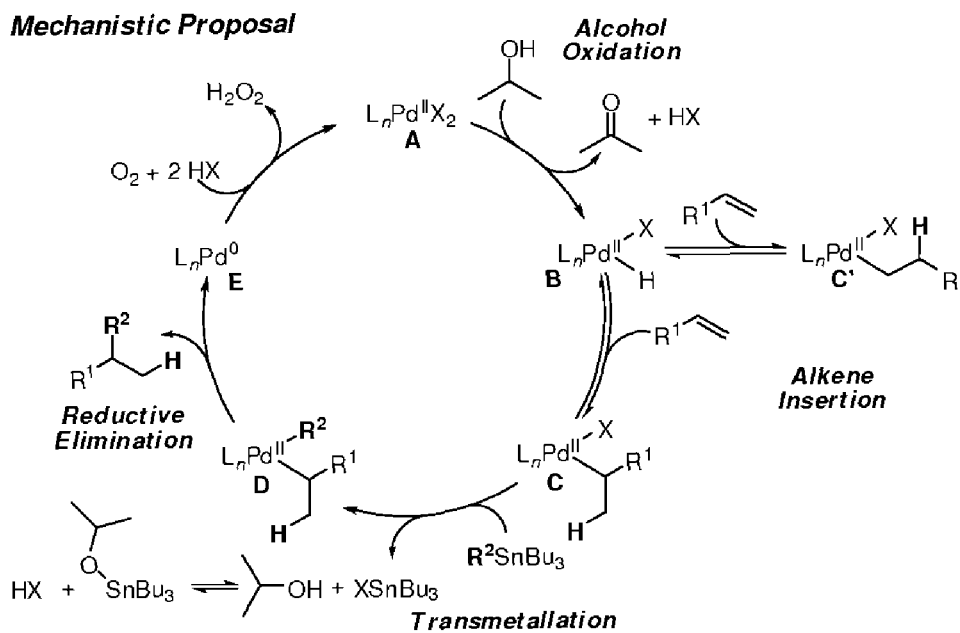
FIG. 1(A) shows a conventional cross coupling reaction scheme and the reductive cross coupling reaction scheme.
FIG. 1(B) shows a reductive cross coupling for tandem alcohol oxidation/olefin functionalization in accordance with one embodiment of the present invention.
FIG. 1(C) shows a competitive undesirable oxidative Heck reaction pathway.

FIGS. 4a and 4b are graphs showing: a) The amount of butan-2-one and hydroarylation product generated compared to styrene consumed over time measured by GC based upon 1 equiv. of 1a; ■: 4-methylstyrene (1a), •: hydroarylation (3a), ∆: butan-2-one (5). b) The quantity of boronic ester consumed compared to phenol, hydroarylation product, and biphenyl produced over time; ▼: boronic ester (2a), X: phenol (6), •: hydroarylation (3a), ◦: biphenyl (7).

FIG. 5 shows the reaction of $[Pd(SiPr)Cl_2]_2$ and (−)-sparteine yields complex 8 $[(MH)^+=801.36]$ characterized by ESI-MS in accordance with the present invention.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and "the" include plural referents unless the context clearly dictates otherwise. Thus, for example, reference to "an additive" includes one or more of such additives, reference to "a reaction" includes reference to one or more of such events, and reference to "introducing" includes reference to one or more of such steps.

As used herein, the term "substantially" or "substantial" refers to the complete or nearly complete extent or degree of an action, characteristic, property, state, structure, item, or result. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" electrophilic coupling partners would either completely lack such compounds, or so nearly completely lack such that the relevant effect would be the same as if it completely lacked the same. In other words, a composition that is "substantially free of" an ingredient or element may still contain such an item as long as there is no substantially measurable difference on the result of interest.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 micron to about 5 microns" should be interpreted to include not only the explicitly recited values of about 1 micron to about 5 microns, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described. As an example, the term "about" also includes "exactly" consistent with the above guidance and without unduly limiting equivalents which would otherwise be available.

EMBODIMENTS OF THE INVENTION

As a general guideline, the present invention can include a reductive cross coupling reaction process for functionalization of a nucleophilic alkene. In particular, the nucleophilic alkene and a nucleophilic cross coupling partner compound can be reacted in the presence of an oxidizable alcohol and a suitable catalyst to form a reductive coupling product. Specifically, the present invention provides methods, systems, and compositions using a reductive cross coupling reaction process for functionalization of nucleophilic alkenes using an oxidizable alcohol and a suitable catalyst.

A reductive cross coupling reaction wherein R—Pd$^{II}$—X originates from a nucleophilic alkene, a common and attractive starting material in organic synthesis, instead of an electrophilic organic reagent (FIG. 1A) is provided. Based on Pd$^{II}$-catalyzed alcohol and olefin oxidations, this approach can be accomplished by a tandem alcohol oxidation/olefin functionalization sequence. Specifically, and without being bound to any particular theory, oxidation of an alcohol solvent (in this case 2-propanol) with a Pd-catalyst A can lead to the formation of a Pd$^{II}$-hydride B as shown in FIG. 1B. Insertion of the olefin into the Pd$^{II}$-hydride will yield a Pd$^{II}$-alkyl intermediate C (or C'). Transmetallation to form D and subsequent reductive elimination provides the reductive coupling product as well as the reduced catalyst E. Aerobic oxidation of Pd$^0$ to Pd$^{II}$ completes the catalytic cycle. The reductive coupling product contains a new sp$^3$ hybridized carbon atom which is significantly more challenging to incorporate than sp or sp$^2$-hybridized carbons resulting from conventional cross coupling type reactions. Many pitfalls were anticipated in developing this reductive cross coupling reaction including the possibility of competitive oxidative Heck products formed by initial transmetallation of the organometallic reagent with a Pd$^{II}$ catalyst (FIG. 1C). As such, the present invention describes the design and development of a Pd$^{II}$-catalyzed reductive cross coupling reaction of alkenes and organostannanes coupled to the aerobic oxidation of a simple alcohol.

A reductive cross coupling reaction process for functionalization of a nucleophilic alkene can comprise reacting the nucleophilic alkene and a nucleophilic cross coupling partner compound in the presence of an oxidizable alcohol and a catalyst to form a reductive coupling product. Each of these components can be carefully chosen based on the following summary and detailed description.

The nucleophilic alkene can be chosen based on the desired final product, as substantially the entire molecule is incorporated into the reductive coupling product. Suitable nucleophilic terminal alkenes can have the general formula:

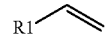

where R1 can be almost any suitable compound such as but not limited to aromatic and/or aliphatic compounds. Additionally, suitable internal alkenes can have the general formula

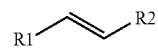

where R2 can be almost any suitable compound such as but not limited to aromatic and/or aliphatic compounds. Even though the internal alkene general formula has been shown in a trans configuration, the cis configuration can also be used; i.e.,

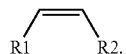

Additionally, mixtures of terminal and internal alkenes can also be used with the embodiments described herein. As such, any nucleophilic alkene can be used as long as other moieties present in the compound do not interfere with the cross coupling reaction. In one embodiment, terminal alkenes have shown particularly effective performance as presented in more detail below.

In addition to considerations of interference with the cross coupling reactions, nucleophilic alkenes can be suitable as long as they do not cause undesirable side reactions as described in more detail below. In one specific aspect, the nucleophilic alkene can be selected from the group consisting of polycyclic aromatic alkenes, monocyclic aromatic alkenes, heterocyclic aromatic alkenes, non-aromatic alkenes, and combinations thereof.

As the second contributor of the cross coupling reaction, a nucleophilic cross coupling partner can be chosen having the desired functional groups to be associated with the nucleophilic alkene. Although a wide variety of cross coupling partners can be suitable, non-limiting examples of such materials can include organostannanes, organozinc reagents, organosilanes, boronic acid derivatives, and combinations thereof. In one specific aspect of the present invention, the nucleophilic cross coupling partner can be an organostannane. Although relative quantities can vary, the nucleophilic cross coupling partner compound can be present in approximate stoichiometric amounts.

One particular aspect of the present invention is the presence of an oxidizable alcohol which acts as a hydrogen source during the desired reactions, among other benefits. Almost any oxidizable alcohol which does not interfere with the cross coupling reaction can be useful. However, as a general rule, the oxidizable alcohol can be a simple C1-C10 straight or branched alcohol. Non-limiting examples of suitable oxidizable alcohols can include isopropyl alcohol, C1-C5 straight or branched alcohols, primary or secondary benzylic alcohols, and combinations thereof. In one currently desirable aspect, the oxidizable alcohol can be isopropyl alcohol. The amount of oxidizable alcohol is sufficient to drive the cross coupling reaction predominantly, and preferably substantially exclusively, along a reductive pathway rather than an oxidative pathway, e.g. Heck pathway. Acceleration of the oxidation of the alcohol can be accomplished by addition of exogenous bases. As such, the present processes described herein can further include an exogenous base. In one embodiment, the exogenous base can be, without limitation, (−)-sparteine, potassium tert-butoxide, triethylamine, Hünig's base, Tröger's base, 2,6-lutidine, 1,8-Diazabicyclo[5.4.0]undec-7-ene (DBU), any amine bases including tertiary, cyclic, aromatic, any inorganic base such as, KOiPr, NaOiPr, KOEt, NaOEt, $Cs_2CO_3$, $K_2CO_3$, $KHCO_3$, $Na_2CO_3$, CsF, $CuF_2$, $CuCl_2$, $Cu(OAc)_2$, and mixtures thereof. Although exact proportions can vary from system to system, as a general guideline the oxidizable alcohol can be present in generous stoichiometric excess.

The reactions of the present invention are catalytically driven via a suitable catalyst. Non-limiting examples of suitable catalysts can include palladium, cerium, rhodium, platinum, cobalt, ruthenium, nickel, and compounds, combinations, intermetallics, and alloys thereof. In one specific aspect of the present invention, the catalyst can be a palladium catalyst. For example, the palladium catalyst can be provided using Pd[(−)-sparteine]Cl$_2$. In yet another alternative, the catalyst can be supported by a suitable catalyst support material. In one embodiment, the palladium catalyst has the following structure:

where L is a ligand, n is any integer from 0 to 2, and X is a halogen, e.g. Br, F, Cl, or I. Additionally, the ligand is selected from the group consisting of (bis)-oxazolines, heterocycle derived oxazolines, $^t$Bu-quinox (2-[(4S)-4-(1,1-dimethylethyl)-4,5-dihydro-2-oxazolyl]-quinoline), chiral phosphines, chiral N-heterocyclic carbenes, chiral tertiary amines, hindered tertiary amines, carbonate bases, chiral carboxylates, and combinations thereof. In one embodiment, the ligand can be, without limitation, IiPr (1,3-Bis(2,6-di-1-propylphenyl)imidazol-2-ylidene), SiPr (1,3-Bis(2,6-di-1-propylphenyl)-4,5-dihydroimidazol-2-ylidine), (−)-sparteine, or mixtures thereof.

In connection with the present invention, various additives can be useful to refine the process such as by mitigating certain undesirable intermediates, facilitating specific site selectivity for various substitutions or reaction sites, etc. In some embodiments, the step of reacting can further include an additive which is a peroxide suppression agent or a chiral additive. A peroxide suppression agent such as $MnO_2$ can be useful in some cases. Of particular interest are additives which act to provide asymmetric catalysis, e.g. allow for regioselective and stereoselective production of reductive coupling products. This can be particularly advantageous in the area of synthesis of pharmaceuticals where stereoisomers and enantiomers can exhibit dramatically different biological activity. Suitable chiral additives can include, but are not limited to, heterocycle derived oxazolines, $^t$Bu-quinox, chiral phosphines, chiral tertiary amines, chiral N-heterocyclic carbenes, hindered tertiary amines, carbonate bases, and combinations thereof. In one specific aspect of the present invention, the chiral additive can be $^t$Bu-quinox.

Regardless of the use of a chiral additive, the reductive coupling products of the present invention can include an sp$^3$ hybridized carbon linking the reductive coupling product together. Specifically, the sp$^3$ hybridized carbon can correspond to a carbon of the reactive alkene carbon pair in the nucleophilic alkene. This results in a substantially increased ability to control formation of specific isomers, whether structural, enantiomeric, or stereoisomeric.

Although the specific mechanism can be adjusted in accordance with the principles of the present invention, one embodiment follows a reductive cross coupling pathway. Such a reductive cross coupling pathway can include oxidizing the oxidizable alcohol to form a catalyst hydride. For example, in one embodiment, the step of oxidizing the oxidizable alcohol to form a catalyst hydride can be by the following reaction schematic:

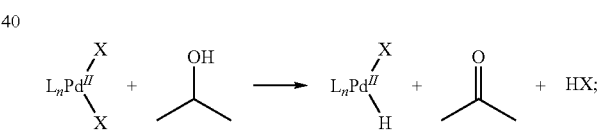

where L is a ligand, n is any integer from 0 to 2, and X is a halogen. The nucleophilic alkene can be inserted into the catalyst hydride to form a catalyst-alkyl intermediate. For example, in one embodiment, the step of inserting the nucleophilic alkene into the catalyst hydride to form a catalyst-alkyl intermediate is by the following reaction schematic:

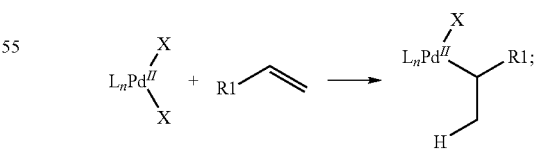

where L is a ligand, n is an integer from 0 to 2, X is a halogen, and R1 is any aryl or alkyl group including mixtures and derivatives thereof which do not materially interfere with the steps described herein. Further, the catalyst-alkyl intermediate can be transmetallated with the nucleophilic cross coupling partner compound to form a transmetallated intermediate. For example, in one embodiment, the step of transmetallating of the catalyst-alkyl intermediate with the nucleophilic cross coupling partner compound to form a transmetallated intermediate is by the following reaction schematic:

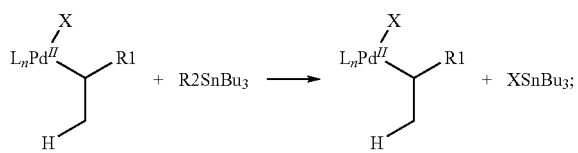

where L is a ligand, n is an integer from 0 to 2, X is a halogen, and R1 and R2 are independently any aryl or alkyl group including mixtures and substitutions thereof. The catalyst can be reductively eliminated to form the reductive coupling product and a reduced catalyst. For example, in one embodiment, the step of reductively eliminating the catalyst to form the reductive coupling product and a reduced catalyst is by the following reaction schematic:

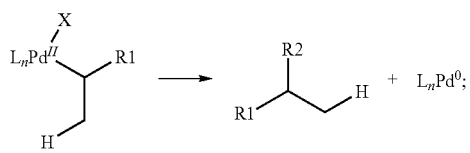

where L is a ligand, n is an integer from 0 to 2, and R1 and R2 are independently any aryl or alkyl group including mixtures and substitutions thereof. Additionally, the reduced catalyst can be oxidized with a variety of oxidants including benzoquinone, inorganic peroxides, organic peroxides, peroxyacids, hypervalent iodide, aryl halides, and molecular oxygen to form the oxidized catalyst and subsequent repetition through the cyclic pathway. For example, in one embodiment, the step of oxidizing the reduced catalyst with oxygen to form the catalyst is by the following reaction schematic:

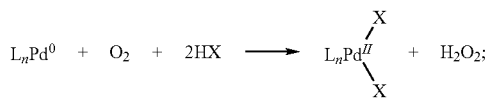

where L is a ligand, n is an integer from 0 to 2, and X is a halogen. FIG. 1, scheme B illustrates one specific example of such a reductive cross coupling pathway using palladium as the catalyst, a terminal alkene, an organostannane, and isopropyl alcohol as the oxidizable alcohol.

The reductive coupling products formed by the process of the present invention can provide highly useful starting materials for synthesis of various compounds such as, but not limited to, biologically active compounds, specialty compounds, and the like. Such reductive coupling products can also be optionally highly optically isomerically pure and can form substantially enantiopure products and in some cases predominantly one enantiomer, i.e. enantioenriched.

Additionally, the present processes described herein can be conducted under conditions sufficient to minimize reaction along an oxidative Heck reaction pathway, or even substantially eliminate reaction along an oxidative Heck reaction pathway. In one embodiment, the minimization can be quantitatively measured by producing an oxidative Heck reaction product of less than 5% yield.

The present invention provides for reductive coupling products that can be formed by the processes described herein. Additionally, a reactor system can include a nucleophilic alkene, a nucleophilic cross coupling partner compound, an oxidizable alcohol, and a catalyst.

EXAMPLES

While the following examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

Example 1

Hydroarylation Using a Reductive Cross Coupling Reaction Process for Functionalization of a Nucleophilic Alkene Careful selection of the catalyst and solvent can facilitate alcohol oxidation and avoid secondary reactions of the solvent with the olefin. Therefore, Pd[(−)-sparteine]Cl$_2$, which has previously shown to be a robust catalyst for both olefin and alcohol oxidations, was selected as a particularly suitable catalyst. An inexpensive solvent, 2-propanol, was chosen since secondary alcohols are good substrates for alcohol oxidation and are less likely to undergo Pd-catalyzed reactions with olefins directly. A styrene (alkene) substrate was initially evaluated due to the inability of the alkene to isomerize and PhSnBu$_3$ was used as the initial cross-coupling partner because additives are not required to facilitate transmetallation of organostannanes.

TABLE 1

Optimization of reaction conditions for reductive coupling product 3a.

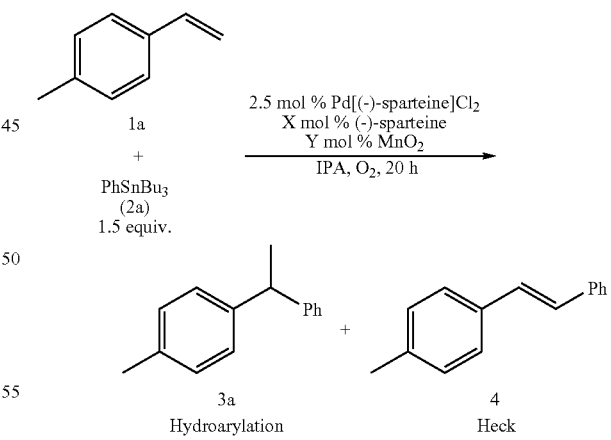

| Entry | Scale$^a$ | X | Y | O$_2$ | Temp. | % Conv.$^b$ | % 3a$^c$ | 3a:4$^d$ |
|---|---|---|---|---|---|---|---|---|
| 1$^e$ | 0.2 | 0 | 0 | balloon | rt | 85 | 23 | 1.3:1 |
| 2 | 0.2 | 0 | 0 | balloon | rt | 67 | 23 | 2.4:1 |
| 3 | 0.2 | 40 | 0 | balloon | rt | 40 | 17 | 28:1 |
| 4 | 0.2 | 40 | 0 | balloon | 60° C. | 63 | 45 | 27:1 |
| 5$^f$ | 0.2 | 20 | 0 | balloon | 60° C. | 37 | 30 | 12:1 |
| 6$^f$ | 0.2 | 40 | 0 | balloon | 60° C. | 30 | 22 | 7.4:1 |
| 7 | 0.2 | 40 | 75 | balloon | 60° C. | >99 | 81 | 35:1 |
| 8$^f$ | 0.2 | 40 | 75 | balloon | 60° C. | 26 | 19 | 7.7:1 |
| 9 | 1.0 | 40 | 0 | balloon | 60° C. | 40 | 24 | 16:1 |

TABLE 1-continued

| | | | | | | | | |
|---|---|---|---|---|---|---|---|---|
| 10[g] | 1.0 | 40 | 0 | 25 psi | 60° C. | 63 | 46 | 26:1 |
| 11[g] | 1.0 | 40 | 75 | 25 psi | 60° C. | 94 | 86 | 22:1 |

[a]Scale in mmol.
[b]Percent conversion measured by GC using an internal standard.
[c]GC yield.
[d]Ratio of GC yields.
[e]7.5 mol % CuCl$_2$ was added.
[f]20 mol % (−)-sparteine-N-oxide was added.
[g]Reaction was performed in a sealed thick-wall glass pressure vessel.

Using this combination of reagents under aerobic conditions, the desired hydroarylation product 3a as >25:1 mixture of regioisomers albeit in low yield (Table 1, entry 1) was obtained. As expected, the major byproduct 4 is formed via an oxidative Heck reaction which is proposed to originate from initial transmetallation of the Pd$^{II}$-catalyst. In contrast, the hydroarylation product 3a is thought to be formed by insertion of the olefin into the Pd-hydride followed by transmetallation (FIG. 1B). Therefore, a decrease in the relative rate of initial transmetallation with respect to the rate of alcohol oxidation was desired to improve the selectivity of the reaction. Addition of Cu salts to Pd$^0$-catalyzed Stille couplings can facilitate transmetallation, while CuCl$_2$ was removed leading to a decrease in conversion presumably due to catalyst decomposition (Table 1, entry 2). However, as the ratio of the hydroarylation product to Heck was improved, Cu-free conditions can also be achieved. Without CuCl$_2$ to help facilitate catalyst regeneration, the aerobic Pd[(−)-sparteine]Cl$_2$-catalyzed oxidation of alcohols, which shows a significant rate enhancement and improved catalyst stability when exogenous (−)-sparteine can be used. Therefore, addition of 40 mol % exogenous (−)-sparteine was evaluated and found to significantly increase the selectivity for the hydroarylation product with a ~28:1 ratio in modest conversion (Table 1, entry 3). To increase the reaction rate, the temperature was raised to 60° C. and a 45% GC yield of the hydroarylation product was observed (Table 1, entry 4).

A time course analysis of the reaction revealed a significant retardation of the rate as the reaction progressed (50% conversion of 1a at 2 h, 65% conversion at 10 h) indicating either catalyst decomposition or inhibition. One possible inhibitor is (−)-sparteine-N-oxide, which can be formed by oxidation of (−)-sparteine with H$_2$O$_2$, a product of O$_2$ reduction. To test our hypothesis, two experiments were performed with added 20 mol % (−)-sparteine-N-oxide at two different concentrations of (−)-sparteine. In both cases, a similar decrease in the conversion of 1a was observed (compare entries 4-6), which is consistent with a detrimental effect of (−)-sparteine-N-oxide (entry 6). Therefore, MnO$_2$ was evaluated as an additive to disproportionate H$_2$O$_2$. Excitingly, addition of 75 mol % MnO$_2$ produced 3a in 81% GC yield at nearly complete conversion (entry 7). Finally, as a control, both MnO$_2$ and (−)-sparteine-N-oxide were added with results similar to the absence of MnO$_2$ (entry 8). To further probe the role of MnO$_2$, ESI-MS was used to analyze the reaction mixtures for the presence of (−)-sparteine-N-oxide. With added MnO$_2$, the ratio of peak heights (which are dependent on ionization potential and do not directly reflect the absolute amount of each species) of (−)-sparteine-N-oxide to (−)-sparteine was found to be 0.50 compared to 0.64 in the absence of MnO$_2$, a ~28% difference. This is consistent with MnO$_2$ acting as a scavenger of H$_2$O$_2$.

Another issue observed upon scaling the reaction was poor conversion of 1a, which was attributed to catalyst decomposition, presumably due to poor mass transport of O$_2$ (entry 9). Raising the pressure of O$_2$ from balloon (~1.1 atm) to 25 psi (1.7 atm) improved the reaction outcome (entry 10). Even with the increased O$_2$ pressure, MnO$_2$ was still required to achieve effective catalysis (compare entries 10 & 11).

With conditions optimized for this embodiment, the initial scope of the Pd$^{II}$-catalyzed reductive coupling was explored. The experimental data shows that the electronic nature of the arylstannane has minimal impact on the yield of the reaction (Table 2, entries 1-7). Substitution ortho on either the styrene or the arylstannane is also tolerated (Table 2, entries 4 and 8). A styrene containing a halogen exhibited high chemoselectivity for the reductive coupling process wherein no products arising from a Stille type coupling were observed (Table 2, entry 5). Acid sensitive groups can also be incorporated (Table 2, entries 6 and 7) and it should be noted that high regioselectivity (>25:1) was observed for all cases in contrast to many of the reported Lewis acid catalyzed hydroarylation reactions. Another aspect of the present process provides an alkene reductive coupling with an organostannane, which allows for expansion to reaction types previously not accessible using reported hydroarylation methods. To this end, several vinyl stannanes were tested under the optimized conditions (Table 2, entries 8-11). Stannanes containing enol ethers were especially competent coupling partners highlighted by the ability to perform an overall hydroacylation reaction (Table 2, entry 10).

TABLE 2

Substrate scope of the Pd$^{II}$-catalyzed reductive coupling of alkenes and organostannanes R$^1$–CH=CH$_2$ + R$^2$SnBu$_3$ → R$^1$CH(R$^2$)CH$_3$ Alkene 1a-f, 1.5 equiv 2a-h 2.5 mol % Pd[(−)-sparteine]Cl$_2$
40 mol % (−)-sparteine
75 mol % MnO$_2$
IPA, 25 psi O$_2$, 60° C., 18 h 3a-k

| Entry | R$^2$ | Product | Yield (%)[a] |
|---|---|---|---|
| 1 | –C$_6$H$_5$ | 3a (Me-C$_6$H$_4$-CH(CH$_3$)-C$_6$H$_5$) | 76 |

TABLE 2-continued

Substrate scope of the Pd$^{II}$-catalyzed reductive coupling of alkenes and organostannanes $$R^1\text{-CH=CH}_2 + R^2SnBu_3 \xrightarrow[\text{IPA, 25 psi O}_2, 60°\text{C., 18 h}]{\begin{array}{c}2.5 \text{ mol \% Pd[(-)-sparteine]Cl}_2\\ 40 \text{ mol \% (-)-sparteine}\\ 75 \text{ mol \% MnO}_2\end{array}} R^1\text{-CH(CH}_3\text{)-}R^2$$

Alkene 1a-f + 1.5 equiv 2a-h → 3a-k

| Entry | R² | Product | | Yield (%)$^a$ |
|---|---|---|---|---|
| 2 | 4-MeO-C₆H₄– | 3b | (4-Me-C₆H₄)CH(Me)(4-MeO-C₆H₄) | 70 |
| 3 | 4-CF₃-C₆H₄– | 3c | (4-Me-C₆H₄)CH(Me)(4-CF₃-C₆H₄) | 67 |
| 4$^b$ | 2-Me-C₆H₄– | 3d | (4-Me-C₆H₄)CH(Me)(2-Me-C₆H₄) | 59 |
| 5 | 4-MeO-C₆H₄– | 3e | (4-Cl-C₆H₄)CH(Me)(4-MeO-C₆H₄) | 65 |
| 6$^c$ | 3,5-(MeO)₂-C₆H₃– | 3f | (4-BocNH-C₆H₄)CH(Me)(3,5-(MeO)₂-C₆H₃) | 58 |
| 7$^{b,c}$ | 3,5-(MeO)₂-C₆H₃– | 3g | (3-OTBS-C₆H₄)CH(Me)(3,5-(MeO)₂-C₆H₃) | 55 |
| 8$^b$ | 3,4-dihydro-2H-pyran-6-yl | 3h | (2-MeO-C₆H₄)CH(Me)(3,4-dihydro-2H-pyran-6-yl) | 63 |
| 9$^b$ | 3,4-dihydro-2H-pyran-6-yl | 3i | (4-Me-C₆H₄)CH(Me)(3,4-dihydro-2H-pyran-6-yl) | 69 |

TABLE 2-continued

Substrate scope of the $Pd^{II}$-catalyzed reductive coupling of alkenes and organostannanes $$R^1\diagup\!\!\!\diagdown + R^2SnBu_3 \xrightarrow[\text{IPA, 25 psi O}_2, 60°\text{C., 18 h}]{\substack{2.5\text{ mol }\% \text{ Pd}[(-)\text{-sparteine}]Cl_2 \\ 40\text{ mol }\% \text{ (-)-sparteine} \\ 75\text{ mol }\% \text{ MnO}_2}} R^1\diagup\!\!\!\diagdown R^2$$

Alkene 1a-f, 1.5 equiv 2a-h, 3a-k

| Entry | $R^2$ | Product | | Yield (%)[a] |
|---|---|---|---|---|
| 10[b,d] | (ethoxyvinyl group) | 3j | (4-methylphenyl propan-1-one derivative) | 52 |
| 11[b] | (isobutenyl group) | 3k | (2-naphthyl prenyl derivative) | 50 |

[a]Average isolated yield of two experiments performed on 1 mmol scale.
[b]3.5 mol % Pd[(−)-sparteine]Cl$_2$ was used.
[c]Reaction was performed on 0.5 mmol scale.
[d]Was treated with HOAc upon work-up.

Example 2

Mechanistic Examination

Figure 2:
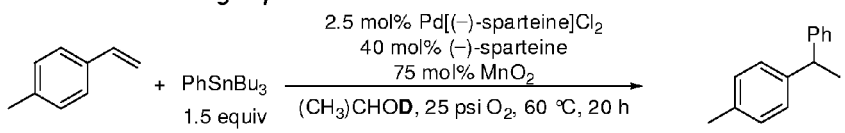
FIG. 2 shows reaction schematics in accordance with the experimental data derived from deuterium labeling experiments showing a proposed mechanism in accordance with one embodiment of the present invention.
Figure 2:
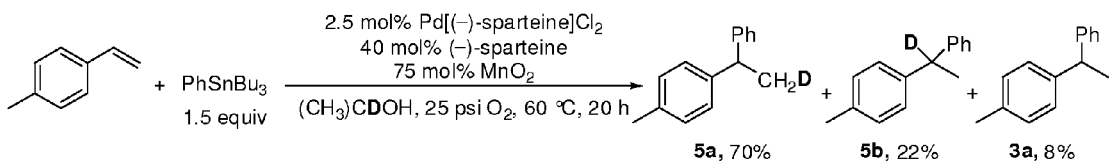
Figure 2:
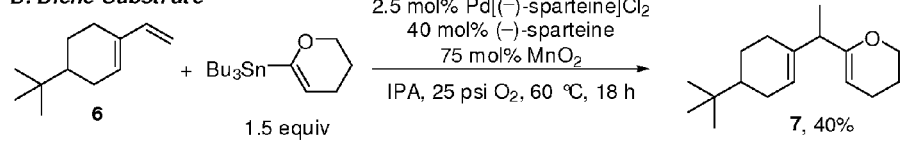
Figure 3:
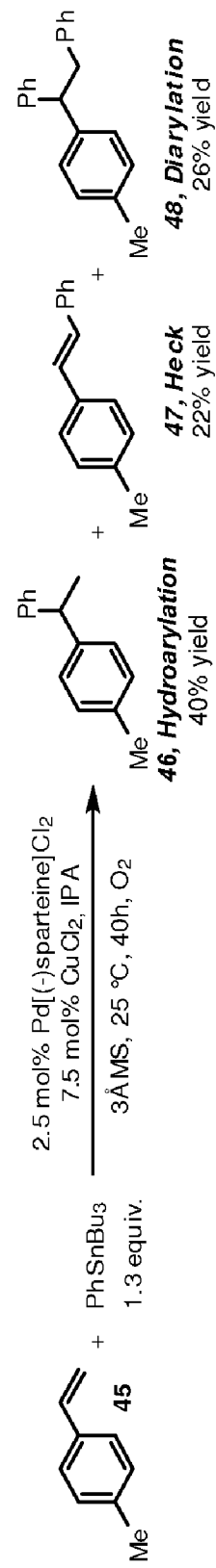
FIG. 3 shows a reaction scheme of hydroarylation of a styrene in accordance with one embodiment of the present invention.

To the initial mechanistic hypothesis provided in FIG. 1B, two isotopic labeling experiments were performed to determine the origin of the proton incorporated into the product (FIG. 2A). When using $(CH_3)_2CHOD$ as the solvent, no deuterium was incorporated into the product ruling out the involvement of acidic protons in the process. However, when using $(CH_3)_2CDOH$ as solvent, 92% of the products contained a single deuterium atom as a mixture of isotopomers 5a and 5b. These data support the mechanistic hypothesis that a coupled alcohol oxidation to form a Pd-hydride is followed by insertion of the olefin into the Pd-hydride (FIG. 1B). The production of two isotopomers supports the reversible formation of both intermediates C and C' from B but the observation of a single product regioisomer suggests only C leads to product. A possible explanation for this is that intermediate C can be stabilized by forming a π-benzyl species when using a styrenyl substrate. A diene substrate was tested which can be similarly stabilized via a π-allyl species (FIG. 2B). This reaction proceeded modestly to yield the reductive coupling product as a single regioisomer and diastereomer. Unfortunately, simple olefins such as decene did not undergo the reductive coupling reaction under these conditions, although conditions may be adjusted and optimized to allow use of decene.

The process of the present invention offers a fundamentally different approach to Pd-catalyzed cross coupling reactions. In this process, $Pd^0$ is not oxidized by the organic substrate but the requisite $Pd^{II}$ organometallic species is accessed via a tandem $Pd^{II}$-catalyzed alcohol oxidation to produce a Pd-hydride followed by alkene functionalization. This contrasting approach allows for the facile highly regioselective formation of $sp^3$-$sp^2$ carbon-carbon bonds with various alkenes and organostannane derivatives. Further, this reductive coupling reaction can be performed under aerobic conditions wherein the reduction of $O_2$ is necessary to complete the catalytic cycle.

Example 3

Extension to Asymmetric Catalysis

The present invention uses organometallic reagents coupled with an alcohol oxidation to provide entry into a regioselective hydroarylation reaction of olefins. Additionally, considering the substantial number of organostannane and boronic acid derivatives readily accessible, successful method development will allow access to diverse, potentially biologically relevant structures, which would be difficult to prepare rapidly otherwise.

Extension to Asymmetric Catalysis.

Based on initial results and the mechanistic hypothesis, asymmetric catalysis can be achieved in accordance with the present invention. There are no reported intermolecular enantioselective hydroarylation reactions of simple olefins with the exception of norbornene. Therefore, the development of asymmetric variants will allow rapid entry into enantiomerically enriched products that are otherwise difficult to access. Two steps can particularly influence asymmetric induction: insertion of the olefin into the Pd-hydride and rate of transmetallation of the resulting diastereomers, as shown in Scheme 3.

Scheme 3.
Mechanistic Hypothesis
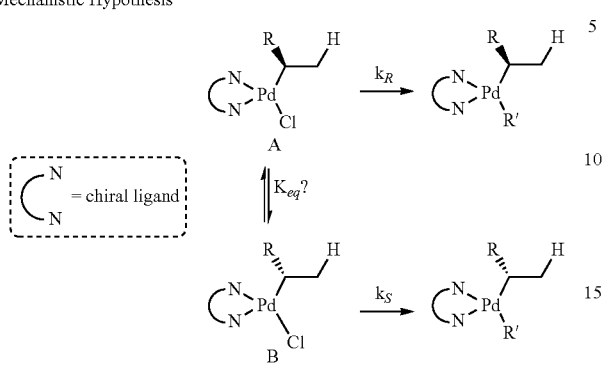
Preliminary Result
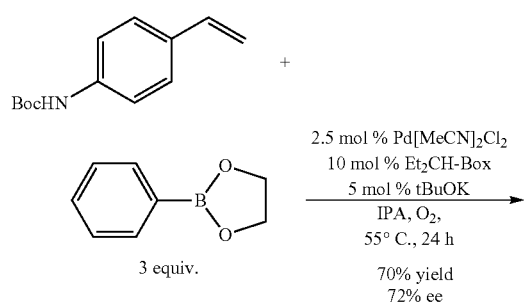
Examples of Chiral N-heterocyclic Amines
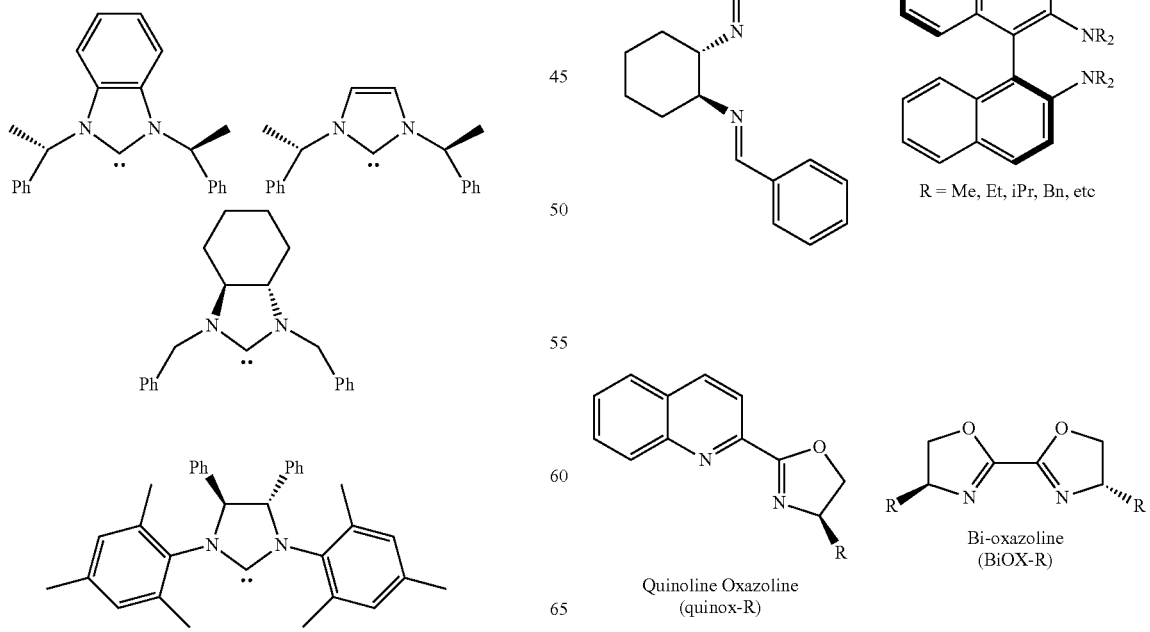
Examples of Chiral Bis-imines and [1,1'-Binaphthalene]-2,2'-diamine Derivatives
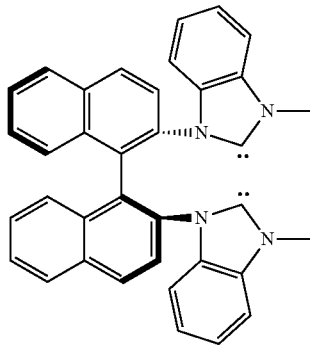
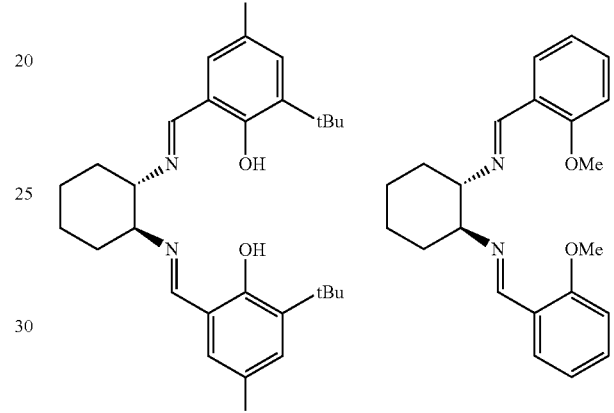

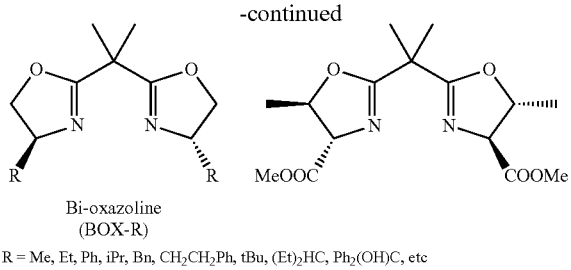

Bi-oxazoline
(BOX-R)

R = Me, Et, Ph, iPr, Bn, CH$_2$CH$_2$Ph, tBu, (Et)$_2$HC, Ph$_2$(OH)C, etc

Examples of Chiral Boronic Ester Derivatives

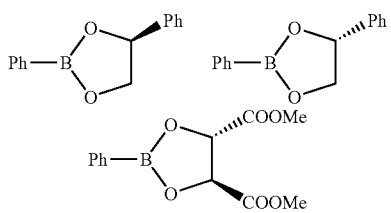

A major question is whether diastereomers A (scheme 3) and B (scheme 3) equilibrate via β-hydride elimination. If rapid equilibration occurs, the relative rates of transmetallation will determine the enantioselective outcome. Chiral ligands are anticipated to have a considerable impact on these rates. Evaluation of a (bis)-oxazoline (Et$_2$CH-Box, see above) under modified conditions led to an observed enantiomeric excess of 72% for 50 (scheme 3). Further optimization by ligand modification is anticipated (see example ligand list above).

Example 4

Extension to Organoboronic Acids & Esters

The Suzuki reaction, which couples an organohalide and an organoboron compound, is a very attractive cross-coupling reaction for use in the synthesis of natural products and pharmaceuticals. This is mainly due to the excellent functional group compatibility and ease of preparation of boronic acid derivatives as well as the low toxicity of the boron byproducts. The mechanistic details have been widely investigated and the reaction is thought to proceed through oxidative addition of the organohalide (R—X) to Pd$^0$ to form R—Pd$^{II}$—X followed by transmetallation of the organoborane (R$^1$—B(OR)$_2$). The resulting R—Pd$^{II}$—R$^1$ intermediate undergoes reductive elimination leading to product formation. An exogenous base is required to activate the boronic acid derivative for transmetallation, which is proposed to occur through a four-centered transition state (Scheme 1a).

An alternative route to generate the requisite R—Pd$^{II}$—X intermediate utilizes an alkene as a synthon for an alkyl-halide. Specifically, styrene derivatives and organostannanes undergo a Pd-catalyzed reductive cross-coupling reaction in isopropyl alcohol (IPA) under an aerobic atmosphere to yield the hydroarylation product 3a in 76% yield (Scheme 1b). The proposed mechanism proceeds via initial oxidation of the alcoholic solvent to generate a Pd$^{II}$-hydride (E), which reacts with the alkene to yield Pd-alkyl F. Subsequent transmetallation forms G and reductive elimination yields the reductive coupling product and Pd$^0$ (H), which is oxidized by O$_2$ to regenerate the active catalyst (D). As discussed above, boronic acids offer significant practical advantages in cross-coupling reactions with respect to organostannane compounds. However, the development of a reductive coupling of alkenes with boronic acid derivatives was thought to be a significant challenge as compared to the use of organostannanes. The reason for this is the requirement of a strong exogenous base to facilitate transmetallation, which will simultaneously affect the rate of alcohol oxidation (Scheme 1b). The addition of base can also promote a base mediated reductive elimination of the proposed Pd$^{II}$-hydride intermediate (E) to form Pd$^0$. Thus, the development of a catalyst system for the reductive coupling of arylboronic esters and styrenes along with studies that highlight the mechanistic complexity of this reaction is provided herein.

Scheme 1:

a) Base Facilitated Transmetalation with Boronic Esters

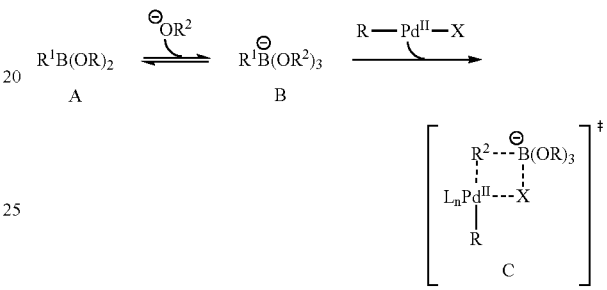

b) Reductive Cross-Coupling Reaction with Stannanes

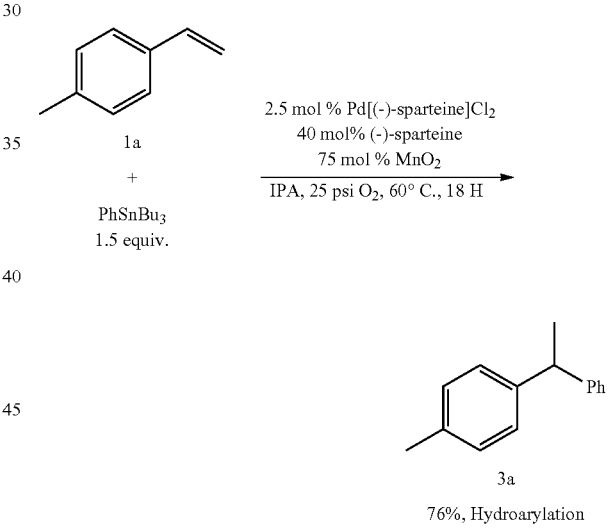

3a

76%, Hydroarylation

Mechanistic Hypothesis

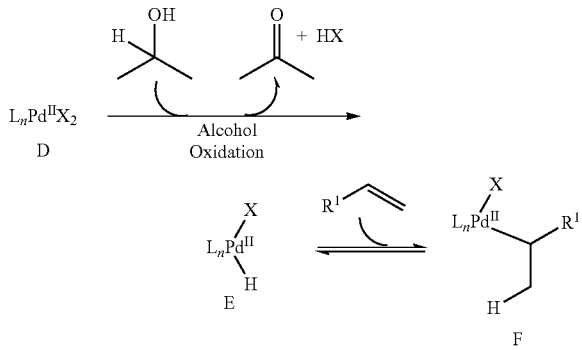

-continued

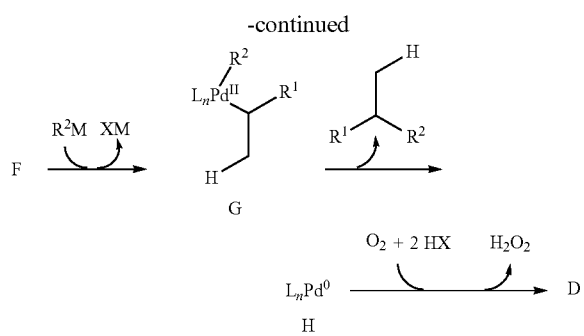

a) Base facilitated transmetallation with boronic esters.
b) Reductive coupling with organostannanes and mechanistic hypothesis.

TABLE 5

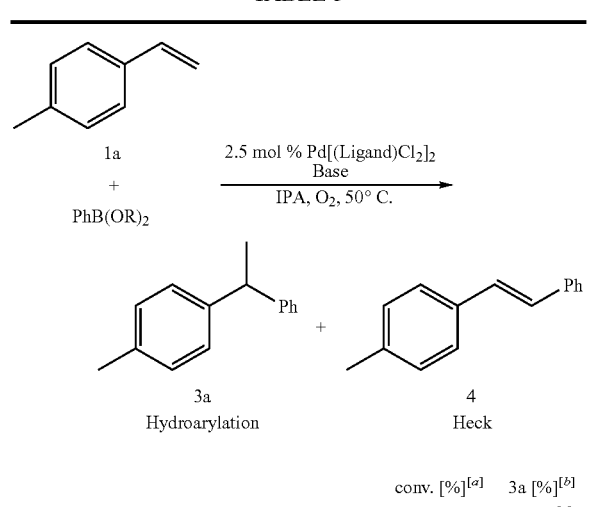

| Entry | Ligand | PhB(OR)$_2$ | Base | conv. [%][a] (time) [h] | 3a [%][b] (3a:4)[c] |
|---|---|---|---|---|---|
| 1[d] | sp | 1.3 equiv of BA | 40 mol % sp | 35 (24) | 11 (1.4:1) |
| 2 | IiPr | 1.3 equiv of BA | 20 mol % sp | 63 (24) | 13 (3.2:1) |
| 3 | IiPr | 1.3 equiv of BA | 20 mol % sp 5 mol % tBuOK | 18 (24) | 8 (6.4:1) |
| 4 | IiPr | 1.3 equiv of PE | 5 mol % sp 5 mol % tBuOK | 99 (24) | 30 (2.7:1) |
| 5 | IiPr | 2.5 equiv of PE | 7.5 mol % sp 7.5 mol % tBuOK | >99 (24) | 64 (17:1) |
| 6 | IiPr | 2.5 equiv of EG | 7.5 mol % sp 7.5 mol % tBuOK | >99 (4) | 49 (27:1) |
| 7 | SiPr | 2.5 equiv of EG | 7.5 mol % sp 7.5 mol % tBuOK | >99 (8) | 68 (>30:1) |
| 8 | SiPr | 2.5 equiv of PD | 7.5 mol % sp 7.5 mol % tBuOK | 46 (24) | 32 (>30:1) |
| 9[e] | SiPr | 3 equiv of EG | 6 mol % sp 6 mol % tBuOK | >99 (24) | 91 (>30:1) |
| 10[e] | IiPr | 3 equiv of EG | 6 mol % sp 6 mol % tBuOK | >99 (24) | 89 (>30:1) |
| 11[f] | sp | 3 equiv of EG | 6 mol % sp 6 mol % tBuOK | >99 (24) | 89 (>30:1) |
| 12[e] | SiPr | 3 equiv of EG | 6 mol % tBuOK | 2 (24) | 1 (4.3:1) |

TABLE 5-continued

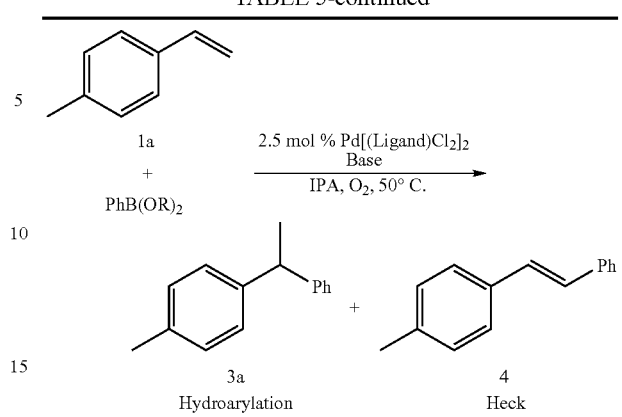

| Entry | Ligand | PhB(OR)$_2$ | Base | conv. [%][a] (time) [h] | 3a [%][b] (3a:4)[c] |
|---|---|---|---|---|---|
| 13[e] | SiPr | 3 equiv of EG | 6 mol % sp | >99 (24) | 78 (23:1) |

[a]Percent conversion measured by GC using an internal standard.
[b]GC yield.
[c]Ratio of GC yields.
[d]2.5 mol % Pd[sp]Cl$_2$.
[e]0.75 mol % [Pd(Ligand)Cl$_2$]$_2$ and 55° C.
[f]1.5 mol % Pd[sp]Cl$_2$ and 55° C.

Ligands                     Boronic Esters

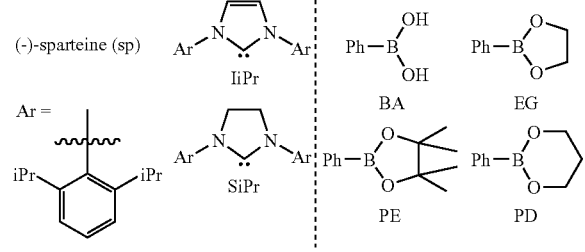

By using the reaction conditions developed for the Pd-catalyzed reductive coupling with organostannanes and the commercially available boronic acid (PhB(OH)$_2$) the desired hydroarylation product (3a) was observed in 11% yield (GC) as a greater than 25:1 ratio of regioisomers (Table 5, entry 1). However, catalyst decomposition and competitive initial transmetalations was observed, which generates the oxidative Heck product (4). The poor stability of [Pd{(−)-sparteine}Cl$_2$] under these conditions prompted us to identify a more robust catalyst system. As previously discussed, Pd complexes with N-heterocyclic carbine (NHC) ligands are excellent catalysts for alcohol oxidation in which high turnover numbers are achieved at low concentrations of O$_2$. Also, Pd(NHC) complexes have been widely employed in a variety of cross-coupling reactions. Thus, [{Pd(IiPr)Cl$_2$}$_2$] was evaluated by using (−)-sparteine (sp) as an exogenous base and an improved ratio of hydroarylation to Heck reaction was observed with only a 63% conversion of the substrate (Table 5, entry 2). The addition of tBuOK led to additional improvement in the ratio of 3a to 4 (Table 5, entry 3). The low conversion of these reactions may arise from PhB(OH)$_2$ inhibiting the catalysis; exogenous acid can decrease the rate of alcohol oxidation. Therefore, the pinacol-derived phenylboronic ester (PE) was submitted to the reaction conditions with both sp and tBuOK, which led to a 30% yield (GC) of 3a (Table 5, entry 4). The reaction was monitored by GC methods and PE was fully consumed before the reaction of the olefin was complete, suggesting that remaining 1a undergoes an undesired reaction that does not involve the boronic ester. On the basis of this hypothesis the amount of PE was increased to 2.5 equivalents to produce 3a in 64% yield (GC) with a 17:1 ratio of 3a to 4 (Table 5, entry 5).

To further optimize the reaction, ethylene glycol-derived boronic ester (EG), which was expected to undergo faster transmetalation because of its smaller size, was submitted to the reaction conditions and a 49% yield (GC) of 3a was measured after 4 hours (Table 5, entry 6). Evaluating other NHC ligands revealed that the combination of SiPr and EG produces 3a in 68% yield within 8 hours (Table 5, entry 7). Interestingly, when propanediol-derived boronic ester PD was used under the same reaction conditions a 32% yield of 3a was observed, demonstrating the sensitivity of the transformation to the nature of the boronic ester (Table 5, entry 8).

Additional optimization of the reaction conditions, including an increase to three equivalents of EG, produces 3a in 91% yield (GC) with [{Pd(SiPr)Cl$_2$}$_2$] as the catalyst; these conditions were found to be the optimal conditions for the transformation (Table 5, entry 9). [{Pd—(IiPr)Cl$_2$}$_2$] is also a proficient catalyst under these conditions yielding 3a in 89% yield (GC) (Table 5, entry 10). Interestingly, under these conditions [Pd(sp)Cl$_2$] is also an effective catalyst (Table 5, entry 11). Finally, the reaction was performed under the optimal conditions without sp, leading to rapid Pd$^0$ metal precipitation with only 2% conversion of 1a (Table 5, entry 12). In contrast, performing the reaction without tBuOK leads to a 78% yield (GC) of 3a, suggesting that the combination of both sp and tBuOK is required to achieve excellent catalysis (Table 5, entry 13). However, the use of more tBuOK led to diminished yields of 3a.

TABLE 6

| Entry | R² | | Product | Yield [%][a] |
|---|---|---|---|---|
| 1 | 2a (phenyl) | 3a | Me-C₆H₄-CH(CH₃)-C₆H₅ | 81 |
| 2 | 2a (phenyl) | 3b | C₆H₅-CH(CH₃)-C₆H₅ | 91 |
| 3 | 2b (4-F-C₆H₄) | 3c | Me-C₆H₄-CH(CH₃)-C₆H₄-F | 78 |
| 4 | 2a (phenyl) | 3d | Boc-NH-C₆H₄-CH(CH₃)-C₆H₅ | 90 |
| 5[b] | 2c (4-dioxolane-C₆H₄) | 3e | Me-C₆H₄-CH(CH₃)-C₆H₄-CHO | 77 |
| 6[b] | 2c (4-dioxolane-C₆H₄) | 3f | Cl-C₆H₄-CH(CH₃)-C₆H₄-CHO | 68 |

Reaction: Alkene 1a-e + R²—B(dioxolane) (3 equiv, 2a-h) → 3a-l; 0.75 mol % [Pd(SiPr)Cl$_2$]$_2$, 6 mol % (−)-sparteine, 6 mol % tBuOK, IPA, O$_2$, 55° C., 24 h

TABLE 6-continued

| Entry | R² | | Product | Yield [%][a] |
|---|---|---|---|---|
| 7[b] | 2d (aryl with 1,3-dioxolane-2-methyl) | 3g | diaryl methane with p-Me and p-acetyl | 71 |
| 8[c] | 2e (p-OMe aryl) | 3h | diaryl methane with p-Me and p-OMe | 58 |
| 9[c] | 2f (p-iPr aryl) | 3i | diaryl methane with phenyl and p-iPr | 65 |
| 10[c] | 2g (o-Me aryl) | 3j | diaryl methane with p-Me and o-Me | 68 |
| 11[d] | 2h (p-CO₂Me aryl) | 3k | diaryl methane with phenyl and p-CO₂Me | 63 |
| 12 | 2a (phenyl) | 3l | 1-phenyl-1-(cyclohexenyl)ethane | 41 |

[a]Average isolated yield of two experiments performed on 0.5 mmol scale.
[b]Was treated with p-toluenesulfonic acid in acetone/H₂O upon work-up.
[c]1.5 mol % [Pd(SiPr)Cl₂]₂ and 65° C.
[d]15 mol % sp.

Diaryl methane units are prevalent in biologically active small molecules and this method can allow the rapid highly regioselective synthesis of this functionality. To explore the scope of the reductive coupling of boronic esters and styrenes, the above conditions were used to synthesize a variety of diaryl methane-containing products (Table 6). All of the reductive coupling reactions are highly regioselective (>25:1), and the reactions of simple coupling partners give high yields (78-91%) of isolated diaryl methane-containing products (Table 6, entries 1-3). The results demonstrate that substrates containing acid-sensitive functional groups are stable to the reductive coupling reaction conditions; for example, acetal protecting groups, which are readily removed upon work up, are compatible with the reaction conditions (Table 6, entries 5-7). Arylboronic esters containing electron-donating groups react more slowly, thereby requiring a higher catalyst loading (Table 6, entries 8 and 9), and ortho substitution on the arylboronic acid is tolerated (Table 6, entry 10). The ester functionality is also compatible, however an increase in [sp] is required to achieve a 63% yield of 3k (Table 6, entry 11). On the basis of our previous mechanistic hypothesis that the formation of a π-benzyl intermediate is responsible for the outstanding regioselectivity, a diene substrate, which can form a similar π-allyl species, was evaluated and yielded the reductive coupling product 3l in 41% yield as a greater than 25:1 mixture of regioisomers (Table 6, entry 12). Under these conditions both vinylboronic esters and simple alkenes, which rapidly isomerize, do not undergo an effective reductive coupling reaction. Even though a chiral additive (sp) is used, less than 5% enantiomer excess (ee) is observed for the product.

After exploring the scope, there were three mechanistic questions to address: 1) what is the efficiency of alcohol oxidation as compared to product formation? 2) why are three equivalents of the arylboronic ester required for good product yields? and 3) why is exogenous sp required for catalysis? To investigate the first question, a higher molecular weight alcohol, sec-BuOH, was used as the solvent in order to use GC analysis to effectively measure the amount of ketone being formed via alcohol oxidation. A time course analysis of the reaction was performed and the GC yields of the hydroarylation product 3a and butan-2-one (5) as well as the percent styrene 1a remaining were plotted as a function of time (FIG. 4a). Initially, the yield of 3a and 5 are equivalent until ~60% conversion, which is consistent with the oxidation of one alcohol directly yielding product. This also suggests that the $Pd^{II}$-hydride formed via alcohol oxidation reacts with the alkene faster than it reductively eliminates. In contrast, as the reaction progresses to higher substrate conversion, the yield of the 5 increases at a rate different than that of product formation. This shows as the concentration of alkene decreases, the $Pd^{II}$-hydride can undergo other competitive reactions including reductive elimination. The GC yield of 3a was 78% in sec-BuOH as compared to 91% in IPA indicating a modest solvent dependence.

The next question investigated was, why are three equivalents of 2a required? Therefore, the fate of the boronic ester was investigated as the reaction progressed (FIG. 4b). Over an equivalent of 2a was consumed at 30 minutes after which a relatively linear decrease in concentration was observed (the scatter can be attributed to hydrolysis of 2a on silica before GC analysis). Besides the hydroarylation product 3a, two major byproducts, biphenyl (6) and phenol (7), derived from the boronic ester were observed. A 10% GC yield of biphenyl, the product of oxidative boronic acid homocoupling, is formed at 2 h, but a 14% yield of biphenyl (~0.28 equiv. of 2a consumed) is observed overall. Phenol is the major byproduct of this reaction and is formed consistently throughout the reaction (~1.3 equiv. of 2a). Phenol is likely formed from the reaction of the boronic ester with $H_2O_2$ formed from the reduction of $O_2$ during catalyst regeneration. Together these data account for the undesired pathways that consume the excess arylboronic ester required.

The final mechanistic question was the role(s) of sp considering that performing the reaction without exogenous sp leads to poor catalysis. Several functions of sp can be envisioned including acting as a ligand to stabilize $Pd^0$ during catalyst regeneration, acting as a ligand on $Pd^{II}$ during the reductive coupling process, and/or to break up the dimeric $[Pd(SiPr)Cl_2]_2$ complex. The first two roles are difficult to directly probe, however an experiment was performed to investigate the feasibility of sp breaking up the dimer complex. The experiment involved dissolving $[Pd(SiPr)Cl_2]_2$ and 2 equiv. of sp in 1,2-dichloroethane (DCE). The resulting mixture was heated to reflux for 2 h (FIG. 5). An aliquot of the mixture was analyzed by ESI-MS. Excitingly, the major Pd-complex observed in solution corresponds to $Pd(SiPr)(sp)Cl_2$ [m/z $(MH)^+$=801.3]. Based upon the trans-geometry of related $Pd(NHC)(pyridine)Cl_2$ complexes, the formation of complex 8 in which the NHC ligand is trans to the monodentate sp ligand is a proposed mechanism. Unfortunately, attempts to isolate complex 8 only led to the $[Pd(SiPr)Cl_2]_2$ complex and free sp. This shows that complex 8 is in equilibrium with the dimer. It should be noted that $Pd[(-)-sparteine]Cl_2$ is not observed by ESI-MS. Interestingly, other simple amine bases do not lead to an effective catalytic system for reductive coupling. Possible explanations for this are the large size of sp facilitates ligand dissociation or the free nitrogen of sp could act as an intramolecular base.

In conclusion, a catalyst system has been developed for a highly regioselective reductive coupling of arylboronic esters and styrenes under aerobic conditions to yield a variety of diaryl methine containing products. The mechanism couples an alcohol oxidation with C—C bond formation, where an alkene can be thought of as an alkyl halide in classic cross-coupling reactions. Careful analysis of the reaction progress reveals why excess arylboronic ester is required for effective catalysis where phenol formed via oxidation of the boronic ester with $H_2O_2$ from $O_2$ reduction is the major byproduct. Also, the requirement of two bases, (−)-sparteine and tBuOK, has been explored revealing that (−)-sparteine may promote the formation of a monomeric catalyst. These principles can be applied to other Pd-catalyzed reductive coupling processes coupled to alcohol oxidation as described herein and extension to asymmetric catalytic variants.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A reductive cross coupling reaction process for functionalization of a nucleophilic alkene comprising:
    a) reacting the nucleophilic alkene and a nucleophilic cross coupling partner compound in the presence of an oxidizable alcohol and a catalyst to form a reductive coupling product.

2. The process of claim 1, wherein the nucleophilic alkene is selected from the group consisting of polycyclic aromatic alkenes, monocyclic aromatic alkenes, heterocyclic aromatic alkenes, non-aromatic alkenes, conjugated dienes, and combinations thereof.

3. The process of claim 1, wherein the nucleophilic cross coupling partner compound is selected from the group consisting of organostannanes, organosilanes, organozinc reagents, boronic acid derivatives, and combinations thereof.

4. The process of claim 3, wherein the nucleophilic cross coupling partner is an organostannane or organoboronic acid/ester.

5. The process of claim 1, wherein the oxidizable alcohol is selected from the group consisting of isopropyl alcohol, C1-C5 straight or branched alcohols, primary or secondary benzylic alcohols, and combinations thereof.

6. The process of claim 5, wherein the oxidizable alcohol is isopropyl alcohol.

7. The process of claim 1, wherein the catalyst is a palladium catalyst.

8. The process of claim 1, wherein the palladium catalyst has the following structure:

where L is a ligand, n is any integer from 0 to 2, and X is a halogen.

9. The process of claim 8, wherein the ligand is selected from the group consisting of heterocycle derived oxazolines, Et₂CH—BOX ((4S,4'S)-2,2'-(propane-2,2-diyl)bis(4-(pentan-3-yl)-4,5-dihydrooxazole) chiral phosphines, chiral N-heterocyclic carbenes, chiral tertiary amines, hindered tertiary amines, carbonate bases, and combinations thereof.

10. The process of claim 8, wherein the ligand is selected from the group consisting of IiPr (1,3-Bis(2,6-di-1-propylphenyl)imidazol-2-ylidene), SiPr (1,3-Bis(2,6-di-1-propylphenyl)-4,5-dihydroimidazol-2-ylidine), (−)-sparteine, or mixtures thereof.

11. The process of claim 1, wherein the step of reacting further comprises an exogenous base.

12. The process of claim 11, wherein the exogenous base is selected from the group consisting of (−)-sparteine, potassium tert-butoxide, triethylamine, Hünig's base, Tröger's base, 2,6-lutidine, 1,8-Diazabicyclo[5.4.0]undec-7-ene (DBU), amine bases including tertiary, cyclic, and aromatic, inorganic bases including KOiPr, NaOiPr, KOEt, NaOEt, Cs₂CO₃, K₂CO₃, KHCO₃, Na₂CO₃, CsF, CuF₂, CuCl₂, Cu(OAc)₂, and mixtures thereof.

13. The process of claim 1, wherein the step of reacting further comprises an additive which is a peroxide suppression agent or a chiral additive.

14. The process of claim 13, wherein the additive is a chiral additive selected from the group consisting of heterocycle derived oxazolines Et₂CH—BOX ((4S,4'S)-2,2'-(propane-2,2-diyl)bis(4-(pentan-3-yl)-4,5-dihydrooxazole), chiral phosphines, chiral N-heterocyclic carbenes, chiral tertiary amines, hindered tertiary amines, carbonate bases, and combinations thereof.

15. The process of claim 14, wherein the chiral additive is Et₂CH—BOX ((4S,4'S)-2,2'-(propane-2,2-diyl)bis(4-(pentan-3-yl)-4,5-dihydrooxazole).

16. The process of claim 13, wherein the additive is a chiral additive selected to provide asymmetric catalysis.

17. The process of claim 1, wherein the step of reacting is conducted under conditions sufficient to minimize reaction along an oxidative Heck reaction pathway by producing an oxidative Heck reaction product of less than 5% yield.

18. The process of claim 1, wherein the step of reacting is conducted under conditions sufficient to substantially eliminate reaction along an oxidative Heck reaction pathway by producing an oxidative Heck reaction product of less than 5% yield.

19. The process of claim 18, wherein the conditions include accelerating oxidation of the oxidizable alcohol.

20. The process of claim 1, wherein the step of reacting substantially follows a reductive cross coupling pathway including at least the following steps:
a) oxidizing the oxidizable alcohol to form a catalyst hydride;
b) inserting the nucleophilic alkene into the catalyst hydride to form a catalyst-alkyl intermediate;
c) transmetallating of the catalyst-alkyl intermediate with the nucleophilic cross coupling partner compound to form a transmetallated intermediate; and
d) reductively eliminating the catalyst to form the reductive coupling product and a reduced catalyst.

21. The process of claim 20, wherein the step of oxidizing the oxidizable alcohol to form a catalyst hydride is by the following reaction schematic:

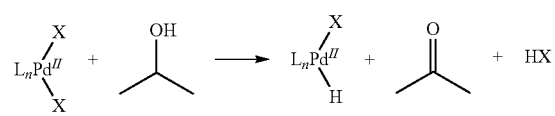

where L is a ligand, n is any integer from 0 to 2, and X is a halogen.

22. The process of claim 20, wherein the step of inserting the nucleophilic alkene into the catalyst hydride to form a catalyst-alkyl intermediate is by the following reaction schematic:

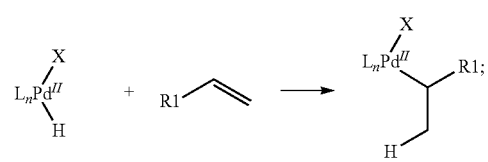

wherein the step of transmetallating of the catalyst-alkyl intermediate with the nucleophilic cross coupling partner compound to form a transmetallated intermediate is by the following reaction schematic:

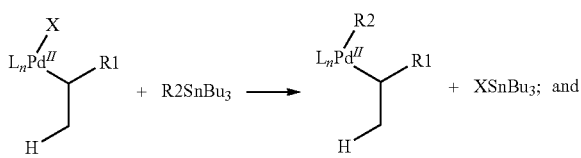

wherein the step of reductively eliminating the catalyst to form the reductive coupling product and a reduced catalyst is by the following reaction schematic:

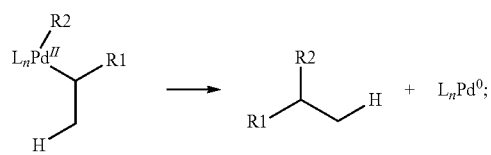

where L is a ligand, n is an integer from 0 to 2, X is a halogen, and R1 and R2 are independently any aryl or alkyl group including mixtures and substitutions thereof.

23. The process of claim 20, further comprising oxidizing the reduced catalyst with oxygen to form the catalyst.

24. The process of claim 23, where the step of oxidizing the reduced catalyst with oxygen to form the catalyst is by the following reaction schematic:

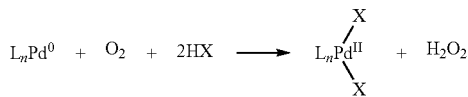

where L is a ligand, n is an integer from 0 to 2, and X is a halogen.

25. The process of claim 1, wherein the reductive coupling product includes an $sp^3$ hybridized carbon linking the reductive coupling product, said $sp^3$ hybridized carbon corresponding to a carbon of the reactive alkene carbon pair in the nucleophilic alkene.

26. The process of claim 1, wherein the nucleophilic alkene includes a terminal alkene, an internal alkene, or mixtures thereof.

27. The process of claim 1, wherein the reacting is performed under aerobic conditions.

* * * * *